United States Patent [19]

Lam et al.

[11] Patent Number: 5,725,572
[45] Date of Patent: Mar. 10, 1998

[54] RADIOPAQUE STENT

[75] Inventors: Sharon S. Lam, San Jose; John J. Frantzen, Copperopolis, both of Calif.; Farhad Khosravi, Newton, Mass.

[73] Assignee: Advanced Cardiovascular Systems, Inc., Santa Clara, Calif.

[21] Appl. No.: 908,906

[22] Filed: Aug. 8, 1997

Related U.S. Application Data

[63] Continuation of Ser. No. 564,936, Nov. 30, 1995, abandoned, which is a continuation of Ser. No. 233,046, Apr. 25, 1994, abandoned.

[51] Int. Cl.⁶ .......................................... A61F 2/06
[52] U.S. Cl. ................ 623/1; 623/12; 606/191; 600/3
[58] Field of Search ............... 623/1, 12; 606/191, 606/194, 198; 600/3

[56] References Cited

U.S. PATENT DOCUMENTS

| | | |
|---|---|---|
| 4,681,110 | 7/1987 | Wiktor . |
| 4,699,611 | 10/1987 | Bowden ........................ 604/51 |
| 4,718,907 | 1/1988 | Karwoski et al. . |
| 4,733,665 | 3/1988 | Palmaz . |
| 4,739,762 | 4/1988 | Palmaz . |
| 4,776,337 | 10/1988 | Palmaz . |
| 4,886,062 | 12/1989 | Wiktor . |
| 4,943,346 | 7/1990 | Mattelin . |
| 5,047,050 | 9/1991 | Arpesani ........................ 623/1 |
| 5,102,417 | 4/1992 | Palmaz . |
| 5,104,404 | 4/1992 | Wolff ........................... 623/1 |
| 5,222,971 | 6/1993 | Willard et al. ................ 606/198 |
| 5,269,802 | 12/1993 | Garber ......................... 623/1 |
| 5,282,823 | 2/1994 | Schwartz et al. ............. 606/198 |
| 5,364,354 | 11/1994 | Walker et al. ................ 604/96 |
| 5,423,849 | 6/1995 | Engelson et al. ............. 606/191 |
| 5,514,154 | 5/1996 | Lau et al. . |
| 5,562,728 | 10/1996 | Lazarus et al. ............... 623/1 |
| 5,649,952 | 7/1997 | Lam ............................ 623/12 |

FOREIGN PATENT DOCUMENTS

| | | |
|---|---|---|
| 0 380 668 A1 | 8/1990 | European Pat. Off. . |
| 0 517 075 A1 | 12/1992 | European Pat. Off. . |
| 0 540 290 A2 | 5/1993 | European Pat. Off. . |
| 2677872 | 12/1992 | France . |

*Primary Examiner*—Paul B. Prebilic
*Attorney, Agent, or Firm*—Fulwider Patton Lee & Utecht, LLP

[57] ABSTRACT

A radiopaque marker associated with a stent which is adapted to be implanted into a patient's body lumen to maintain the patency thereof and a convenient and accurate method for affixing the radiopaque marker to the stent. The radiopaque marker defining an acceptable profile and capable of facilitating, under fluoroscopy, the identification of the position, diameter and length of a stent without obscuring the lesion being repaired and without impeding the deformation of an expandable stent.

10 Claims, 3 Drawing Sheets

RADIOPAQUE STENT

This application is a continuation of Application No. 08/564,936, filed Nov. 30, 1995, now abandoned which is a continuation of Application No. 08/233,046, filed Apr. 25, 1994, now abandoned.

BACKGROUND OF THE INVENTION

This invention relates to endoprosthesis devices, generally called stents, and, more particularly, radiopaque markers for use with endoprosthesis devices.

Stents are useful in the treatment of atherosclerotic stenoses in blood vessels and are generally tubular shaped devices which function to hold open a segment of a blood vessel or other anatomical lumen. They are particularly suitable for use in supporting and holding back a dissected arterial lining which can occlude the fluid passage way therethrough.

In order to accomplish precise placement of stents, various means are employed to identify the position of the stent within a blood vessel. One means frequently described for accomplishing precise placement of a stent is the attachment of radiopaque markers to the stent so that through the use of fluoroscopy, the position of the stent within a blood vessel can be identified. Once the stent with its radiopaque markers has been implanted, subsequent checkups of the treated segment are easily performed since the markers remain visible under fluoroscopy.

Conventional radiopaque markers, however, have various limitations. Upon attachment to a stent, certain conventional radiopaque markers define a profile that is readily discernible from that of the stent, thereby comprising projections which may undesirably alter the contemplated profile of the stent. That is, these conventional radiopaque markers protrude from the walls of the stent and depending upon their location upon the stent, may either project into the blood flow or into the walls of the blood vessel. In addition, these conventional radiopaque markers are limited in that their attachment to the stent can be tedious and imprecise.

Other conventional radiopaque markers restrict the expansion capabilities of an expandable stent by adding rigidity to the stent in areas designated for stent deformation. Still other conventional stents utilize material, such as tantalum, that is effective for use in identifying the location of a stent within a vessel, but fluoroscopically illuminate so brightly so as to obscure proper visibility of the blood vessel lesion, thereby impairing the ability to repair the lesion. Finally, conventional radiopaque markers do not generally, under fluoroscopy, provide the operator with means to accurately assess stent length and diameter.

To overcome the problems and limitations associated with stents having conventional radiopaque markers, it would be desirable to employ radiopaque markers that can be consistently and precisely attached to a stent, that do not limit the expansion capabilities of an expandable stent, that define an acceptable profile, that provide means to assess stent length and diameter and that do not obscure the blood vessel lesion being repaired. The present invention embodies these characteristics.

SUMMARY OF THE INVENTION

The invention provides a radiopaque marker that may be consistently and precisely affixed to a stent, that does not limit the expansion capabilities of an expandable stent, that has an acceptable profile and that may effectively identify the position, diameter and length of a stent within a blood vessel without obscuring a lesion being repaired. The invention also provides means for affixing to a stent a radiopaque marker having the aforementioned characteristics.

The radiopaque marker of the present invention may be utilized with stents having various geometric shapes and materials. In addition, the radiopaque markers may be positioned anywhere on a stent and may comprise any plateable radiopaque material having various patterns. Further, any acceptable means for affixing the radiopaque marker to a stent may be employed. It is essential, however, that the means for attaching a radiopaque marker, its location upon a stent as well as the material and geometric shape of the stent, be selected so that a stent incorporating the radiopaque marker of the present invention may benefit from the advantages provided thereby.

In a preferred embodiment, the radiopaque markers of the present invention are affixed to both a distal and a proximal end of a generally cylindrical stent. In this embodiment, the radiopaque marker material is gold and is affixed to the outside circumference of a generally cylindrical stent by means of plating. Although gold is the designated material of this embodiment, other biocompatible plateable radiopaque materials, such as platinum, are equally desirable. Plating is preferable since it can be performed easily and with accuracy and can be utilized to produce an acceptable radiopaque marker profile. It is contemplated that the thickness of the radiopaque marker material upon a stent be in the range of about 0.0003 to 0.003 inches on the exterior surface of the stent, and if required for fluoroscopic illumination, the same thickness can be plated to the inner stent surface. It is also contemplated that the stent may comprise any material, for example any metal or plastic, upon which gold may be plated.

Although radiopaque material may be plated on only a portion of the circumference of the stent, in a preferred embodiment it is contemplated that the entire circumference of the stent be plated, thereby producing a stent with a band of radiopaque material at its distal and proximal ends. Moreover, it is significant that only the ends of the stent are plated and that gold, or a similarly effective material, may be selected as the plating material. Plating provides controlled deposition of the radiopaque material on the stent thereby controlling its fluoroscopic illumination. By plating only the two ends of the stent, the fluoroscopic illumination is thus limited to the ends of the stent. These two features minimize the possibility of obscuring the fluoroscopic visualization of the blood vessel being treated.

In addition, by plating with radiopaque material at both ends and upon the outside of a generally cylindrical stent, not only can the location of the stent be determined under fluoroscopy, but the length and diameter as well. This is particularly useful where the subject stent is expandable since the degree of expansion can be ascertained by noting the height of the radiopaque marker and the relative distances between the radiopaque markers. Further, it can be determined under fluoroscopy whether or not the stent is twisted or otherwise improperly seated within a blood vessel.

In order to successfully plate gold, or any acceptable radiopaque marker material upon a stent, the stent is placed upon a mandrel, masked and plated. In a preferred procedure, the stent is placed upon an elongated cylindrical mandrel, masked with shrink tubing, portions of which are lased away to expose the areas of the stent desired to be plated and thereafter, plated with the desired radiopaque material. It is contemplated that the mandrel may comprise annular recesses which function to allow portions of an interior circumference of a stent, as well as the exterior of the stent, to be plated.

Subsequent to the completion of the plating procedure, in a preferred procedure the shrink tubing is detached from the stent and the stent removed from the mandrel. It is contemplated that the shrink tubing may be cut from the stent utilizing a laser. Alternatively, the shrink tubing may be dissolved with chemicals. It is also contemplated that the shrink tubing be pre-fabricated or cut to size (by means of a laser) to precise dimensions so that it may properly perform its masking function.

Since a preferred embodiment contemplates gold plating as the avenue for affixing radiopaque markers to a stent and since the gold plating may stiffen the stent in the areas of plating, it is contemplated that expandable stents may be plated in areas where additional rigidity does not affect the expansion capabilities of the stent. Thus, portions of a stent that do not deform upon expansion are plated with gold or the desired radiopaque material. In this way, the stent can freely and uniformly expand and elastically deform without additional restrictions, thereby accomplishing its expansion function while still benefitting from the advantages of the present invention.

In another embodiment, the entire exterior surface of a stent is plated with radiopaque material. Thereafter, the portions designated to retain radiopaque material are masked and the radiopaque material is etched away from the remaining portions of the stent.

In yet another embodiment a generally cylindrical stent is fitted with radiopaque markers having some geometrical configuration or placed upon a stent in some pattern. For instance, a radiopaque marker may comprise a sine wave pattern so that under fluoroscopy, the configuration of the stent may be quickly ascertained. That is, it can be readily ascertained whether the stent is improperly twisted or contorted and in the case of an expandable stent, whether the stent has been properly deformed.

Other features and advantages of the present invention will become apparent from the following detailed description, taken in conjunction with the accompanying drawings, which illustrate, by way of example, the principles of the invention.

DETAILED DESCRIPTION OF THE PREFERRED EMBODIMENTS

As is shown in the drawings, which are included for purposes of illustration and not by way of limitation, the invention is embodied in a radiopaque marker 10 (FIGS. 1A, 1B, 2A, 2B, and 5). Conventional radiopaque markers are limited in that they may comprise undesirable projections extending from a stent, may be arduous to attach, restrict the expansion capabilities of an expandable stent and may be ineffective in the identification of the position, orientation and configuration of a stent. The radiopaque marker 10 of the present invention defines an acceptable, very low profile, may be conveniently affixed to a stent, does not impede the expansion capabilities of an expandable stent, and may be useful in identifying the position, orientation and configuration of a stent within a blood vessel. The radiopaque marker of the present invention, therefore, provides superior means of marking a stent.

The present invention facilitates precise placement of a stent 12 by way of its novel configuration, position upon a stent, and material properties. The characteristics of a radiopaque marker 10 are selected to assure that a stent 12 embodying the radiopaque marker 10 may benefit from the advantages which the invention provides. Thus, radiopaque marker 10 may have various geometric shapes, comprise various materials and may be positioned anywhere on a stent 12, so long as the desired advantages of the invention are achieved.

While stent 12 can include any number of configurations, one preferred embodiment includes a plurality of cylindrical elements 13 which are interconnected so as to be generally aligned on a common longitudinal axis. Stent 12 includes proximal end 14 and distal end 16, and cylindrical elements 13 are attached by one or more connecting elements 17. The connecting elements 17 interconnect the cylindrical elements so that each connecting element 17 connects only cylindrical elements that are adjacent to each other. Each cylindrical element is formed from straight segments 18 connected by curved portions 20 which together form a generally serpentine pattern 21.

In a preferred embodiment, radiopaque marker 10 is plated upon an outer circumference of a generally cylindrical stent 12 and upon a proximal end 14 and a distal end 16 of the stent 12. In another embodiment, it is contemplated that an inner circumference underlying the outer circumference be plated as well. By utilizing plating as the means for affixing radiopaque marker 10 to a stent 12, a minimum profile may be achieved. It is contemplated that the thickness of radiopaque marker 10 be in the range of about 0.0003 to 0.003 inches. As such, the radiopaque marker 10 does not appreciably alter the profile of stent 12 and therefore, does not result in stent 12 having substantial projections extending into the blood flow or into the walls of the blood vessel being repaired.

In addition, by plating or similarly affixing radiopaque material upon a stent, radiopaque markers 10 can be easily and accurately affixed to a stent. That is, plating is an improved means of affixing radiopaque material to stent 12 over conventional means of affixing radiopaque markers, such as sewing or bonding, which can be tedious and imprecise.

Although it is not necessary for all embodiments, the preferred embodiment contemplates that the entire circumference of the stent be plated at both its proximal end 14 and distal end 16. It is also contemplated that the plating material may be gold or a material, such as platinum, which has similar radiopaque characteristics.

It is significant that gold, or a similar material, is contemplated as the preferred radiopaque marker material. Other metals suitable as radiopaque markers include, for example, platinum and silver. By selecting such a material, the stent may be effectively identified under fluoroscopy. In various conventional stents, the radiopaque material employed glows so brightly under fluoroscopy so as to obscure the lesion being repaired. In contrast, the images of radiopaque markers comprised of gold or platinum do not, under fluoroscopy, substantially obscure the lesion being repaired.

Figure 2A:
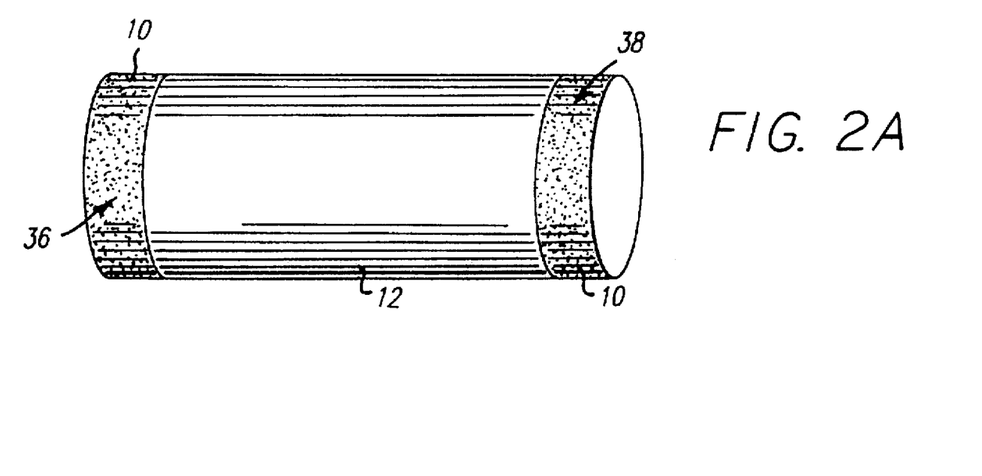
FIG. 2A illustrates a schematic view of a stent embodying radiopaque markers.
Figure 2B:
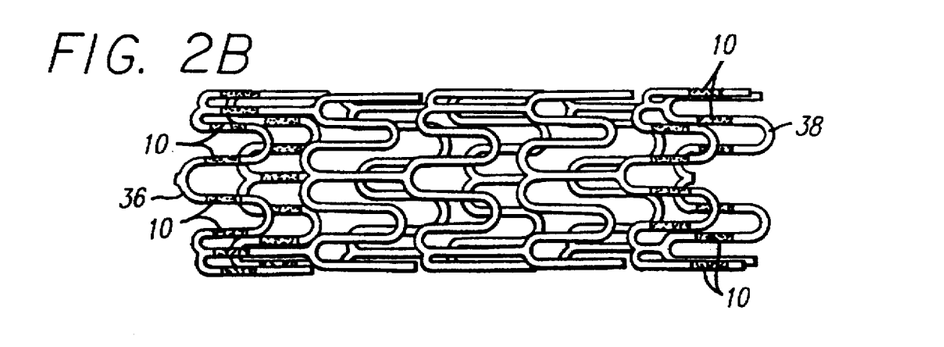
FIG. 2B illustrates a schematic view of another stent embodiment having radiopaque markers.

It is also significant that the preferred embodiment contemplates affixing radiopaque markers 10 to the ends of stents 12 having various geometric configurations (see FIGS. 2A and 2B). By doing so, the orientation or configuration of the stent 12, irrespective of its geometric configuration, can be ascertained, which is particularly important to the determination of whether a stent has completely repaired a blood vessel. By noting the distance between the radiopaque bands, the length of the stent 12 can be ascertained and compared to an expected stent length. By observing the height or width of the radiopaque markers 10, the extent of expansion of an expandable stent 12 can be ascertained and compared with expected values. Similarly, by examining the radiopaque markers of the present invention under fluoroscopy, it can be determined whether the stent 12 is twisted or otherwise improperly seated within a vessel.

Figure 1A:
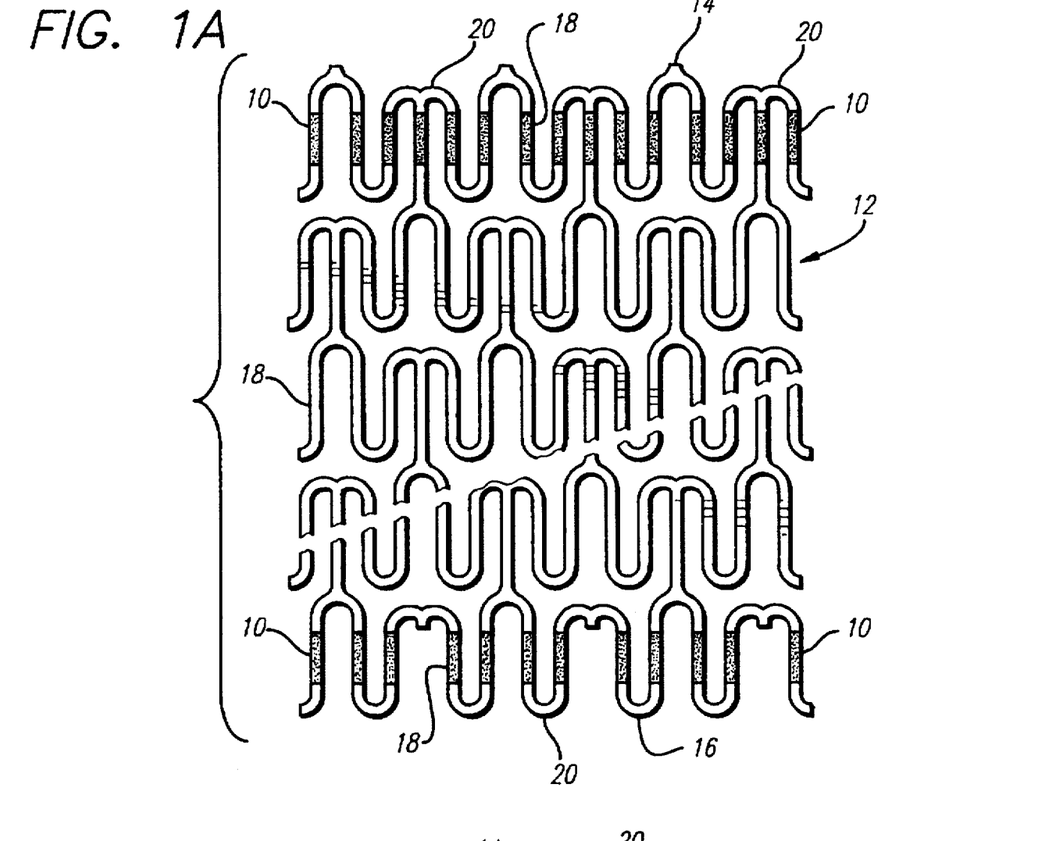
FIG. 1A illustrates a partial view of a stent embodying radiopaque markers.
Figure 1B:
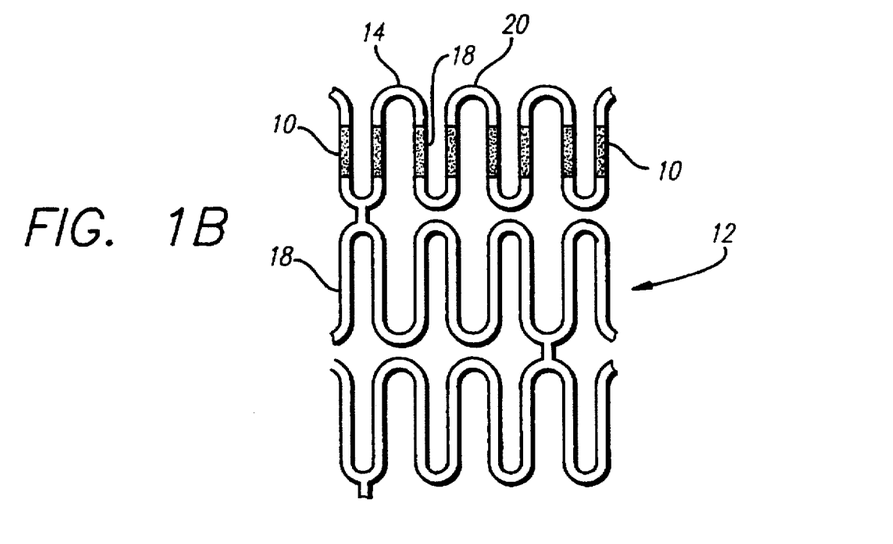
FIG. 1B illustrates a partial view of another stent embodying radiopaque markers.

The plating of radiopaque markers upon a stent may add some rigidity to a stent in the areas of plating. Since this is the case, the preferred embodiment contemplates affixing radiopaque markers 10 to only those portions of an expandable stent 12 that do not deform upon expansion. As shown in FIGS. 1A and 1B for example, radiopaque markers 10 may be affixed to straight segments 18 of the proximal end 14 and distal end 16 of a stent. Upon expansion, the curved portions 20 of the stent 12 may deform so as to allow the stent 12 to expand, while the straight portions 18 may remain undeformed. By affixing radiopaque markers 10 to the straight portions 18 of stent 12 as shown in FIGS. 1A and 1B, the additional rigidity added to the stent 12 by the radiopaque markers 10 does not impede expansion. Therefore, an expandable stent having radiopaque markers 10 of the present invention can uniformly and predictably expand.

Figure 3A:
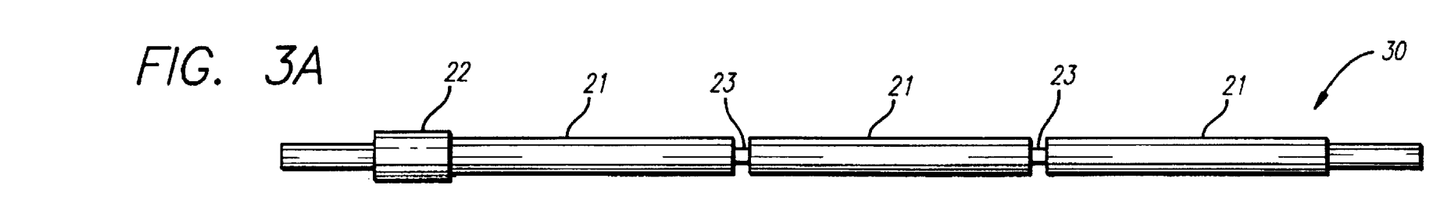
FIG. 3A illustrates a perspective view of a mandrel having annular recesses.
Figure 3B:
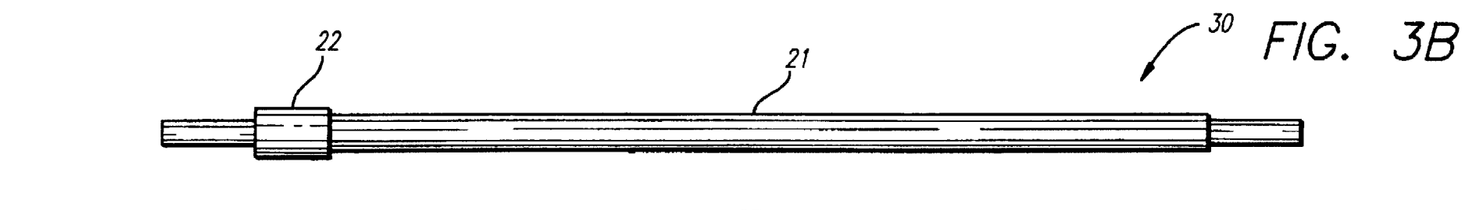
FIG. 3B illustrates a perspective view of a mandrel without annular recesses.

In order to plate a radiopaque marker 10 upon a stent 12, a mandrel 30 may be employed (see FIG. 3A). The mandrel 30 may comprise any suitable material formed into an elongate cylindrical shape having a main portion 21 with a cross-sectional diameter sized for receiving stent 12. The mandrel may further embody a collar 22 formed or attached to one end of the mandrel 30 that has a cross-sectional diameter larger than that of stent 12 and two annular recesses 23 formed in the main portion 21 which have cross-sectional diameters less than that of the main portion 21. The collar 22 functions as a stop and may aid in registering stent 12 upon the mandrel 30. Annular recesses 23 function to allow interior surfaces of stent 12 to be plated. In another embodiment of mandrel 30 (FIG. 3B), recesses 23 may be sufficiently shallow or be missing entirely from mandrel 30 so that, where desirable, interior surfaces of stent 12 are not plated with radiopaque material.

Figure 4A:
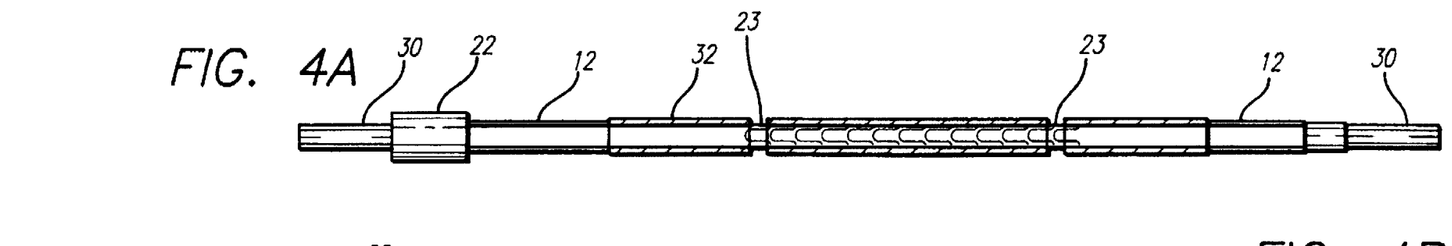
FIG. 4A illustrates a partial cross-sectional view of a masked stent loaded upon a mandrel having annular recesses.
Figure 4B:
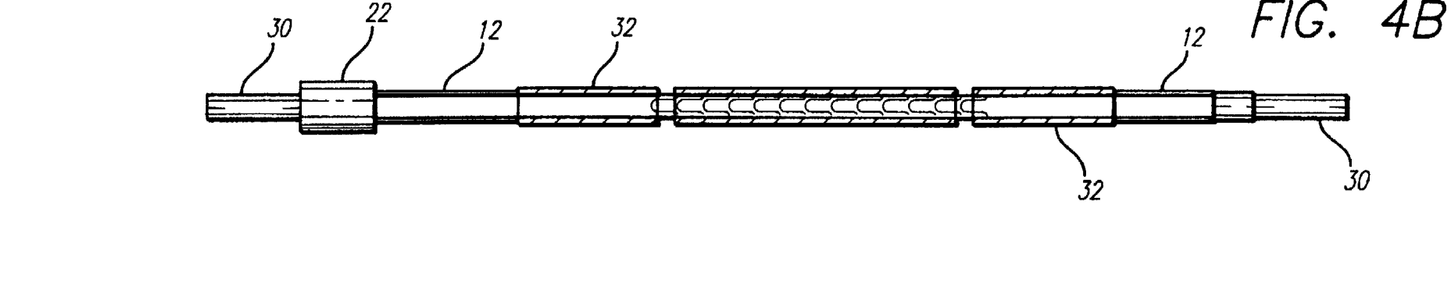
FIG. 4B illustrates a partial cross-sectional view of a masked stent loaded upon a mandrel without annular recesses.

In a preferred method, stent 12 is placed upon mandrel 30 and heat shrink tubing 32 (see FIGS. 4A and 4B) is slipped over stent 12. The heat shrink tubing 32 is then exposed to heat to shrink the tubing on the stent 12. It is contemplated that the heat be concentrated at a midpoint of the heat shrink tubing 32 and then gradually apply heat towards each end so as to prevent distortion of the stent. The shrink tubing 32 may be any polyester having heat shrink properties and the ability to mask the stent during the electroplating process.

Once the heat shrink tubing 32 is snug upon stent 12, the stent may be precisely positioned on the mandrel 30 and then temporarily secured in place using a high temperature wax. Where it is desired to plate an interior as well as an exterior surface of stent 12, the annular recesses 23 may be aligned with the interior portions of the stent 12 desired to be plated (see FIG. 4A). Where it is deemed undesirable to plate the interior surface, no such further alignment is necessary (see FIG. 4B). Next, the curved portions 20 (FIG. 1B) of stent 12 as well as the ends of the mandrel 30 can be dipped in high temperature wax to prevent them from being plated.

In order to plate the desired portions of stent 12, the heat shrink tubing 32 surrounding portions of the stent 12 to be plated may be cut away using a standard $CO_2$ laser or its equivalent. The laser output is to be limited so that stent 12 and mandrel 30 are not affected. By utilizing a mandrel 30 without annular recesses (see FIGS. 3B and 4B), portions of the heat shrink tubing 32 may be lased away so that only the outer circumferences of stent 12 may be plated. By employing the mandrel 30 illustrated in FIGS. 3A and 4A, portions of the heat shrink tubing 32 overlaying annular recesses 23 may be lased away, thereby resulting in a stent 12 having desired portions of its interior as well as its exterior 12 plated with radiopaque material (see FIG. 2B).

As with any electroplating process, an electrical current is used in the process of putting a metallic coating on a metal or other conducting surface. In the preferred embodiment, a gold solution exists in the form of positively charged ions that have lost one or more electrons. The stent is connected to the cathode or negative terminal and the anode, or positive electric terminal, is connected to the stainless steel mandrel 30 which is dipped into the gold solution. The ions are attracted to the cathode and the coating is deposited on the stent metal surface. As is known in the art, the thickness of the layer deposited depends on the amperage of the electric current, the concentration of the metallic ions and the length of time that the stent is plated. The plating process should be at a low enough amperage to prevent mapping, nodules, and a matte surface.

After plating the gold on the stent, the wax is removed from stent 12 and mandrel 30 by inserting them in acetone or an equivalent solution.

As can be appreciated from the drawings (FIGS. 2A and 2B), the end portions 36,38 of a stent 12 which are not masked, are plated with radiopaque material and the portions of the stent 12 which are masked, are not plated.

Once the stent 12 is plated with a radiopaque marker 10, it is removed from the mandrel 30 and the heat shrink tubing 24 is stripped away. The heat shrink tubing 24 may be removed, for example, by cutting it with a laser or in the alternative, dissolved with chemicals. Finally, the mandrel is withdrawn from the plated stent 12 and the stent 12 may be cleaned with an Alcomox or equivalent solution.

In another embodiment, the entire exterior surface of a stent may be plated with radiopaque material. Subsequent to plating, the stent 12 is masked and subjected to etching. In this embodiment, the areas designated to retain radiopaque material are masked and the radiopaque material is etched away from the remaining portions of the stent.

Figure 5:
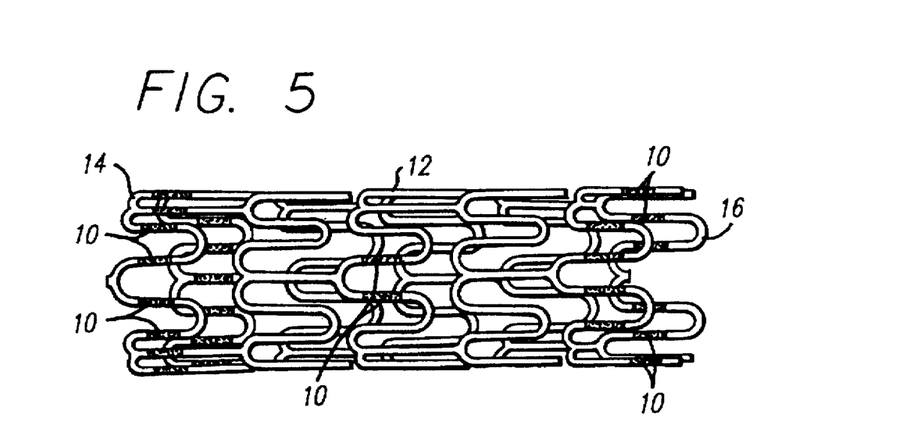
FIG. 5 illustrates a schematic view of the stent having two rows of radiopaque material along the longitudinal axis in addition to the radiopaque material on either end of the stent.

In yet another embodiment, radiopaque markers having some pattern are affixed to a generally cylindrical stent so as to facilitate the identification, position and configuration of a stent 12 within a blood vessel. For example, the pattern of a radiopaque marker 10 may be in the form of a sine wave. As the sine wave expands along with the stent during deployment, it is visible under fluoroscopy and it can be determined whether the stent 12 is properly seated within a blood vessel by viewing the amplitude and shape of the sine wave radiopaque marker. As another example, as depicted in FIG. 5, the pattern of a radiopaque marker 10 may be a continuous or dashed line extending from the proximal end 14 to the distal end 16 of stent 12. A longitudinal marker of the type described will allow the doctor to determine if the stent has twisted upon deployment or if it expanded unevenly.

In an alternative embodiment, a radiopaque plastic may be coated or affixed to all or a portion of a stent. In this embodiment, a radiopaque plastic is formed by loading a plastic material with a radiopaque material such as barium sulfate or bismute trioxide. The resultant mixture is then coated or affixed to the stent. Several methods of affixing the radiopaque material to the stent are contemplated and include: (1) melting the radiopaque material and then dipping the stent into the melt; (2) solvent casting; and (3) vacuum deposition. These methods are generally known and various process steps are apparent to those skilled in the art. As with the plating process steps described above, the stent can be masked and mounted on a mandrel and then coated by dipping, solvent casting, or vacuum deposition.

From the foregoing it will be appreciated that the radiopaque marker of the invention effectively identifies the location and configuration of a stent within a patient's body lumen and provides a method and apparatus for constructing the same.

While several particular forms of the invention have been illustrated and described, it will also be apparent that various modifications can be made without departing from the spirit and scope of the invention. Thus, it should be understood that various changes in form, and detail, and application of the present invention may be made without departing from the spirit and scope of this invention.

What is claimed is:

1. A longitudinally flexible stent having high visibility under fluoroscopy for permanently implanting in a body lumen, comprising:

a plurality of cylindrical elements which are interconnected so as to be generally aligned on a common longitudinal axis;

at least one connecting element for interconnecting the cylindrical elements, the at least one connecting element configured to interconnect only the cylindrical elements that are adjacent to each other;

the plurality of cylindrical elements formed into a serpentine pattern including a plurality of peaks and valleys;

the stent further being constructed of deforming components that undergo deformation upon expansion of the stent and components that remain undeformed upon expansion of the stent; and a radiopaque material exclusively affixed to portions of the undeformed components at least at the distal end and the proximal end of the intravascular stent so that the radiopaque material is visible under fluoroscopy and the distal stent end and the proximal stent end can be easily located in the body lumen where the stent is implanted.

2. The stent of claim 1, wherein the plurality of peaks and valleys comprise curved portions separated by straight segments which extend between the curved portions, the radiopaque material being affixed to the straight segments which comprise the undeformed components when the stent is expanded.

3. The stent of claim 1, wherein the radiopaque material comprises a metal selected from the group of metals consisting of gold, platinum and silver.

4. The stent of claim 1, wherein the radiopaque material has a thickness in the range of approximately of 0.0003 to 0.003 inch.

5. The stent of claim 1, wherein the radiopaque material is attached to all undeformed components of the distal end and the proximal end of the stent.

6. The stent of claim 1, wherein the radiopaque material forms a pattern.

7. The stent of claim 6, wherein the pattern comprises a wave shape.

8. A longitudinally flexible stent having high visibility under fluoroscopy for permanently implanting in a body lumen, comprising:

a plurality of cylindrical elements which are interconnected so as to be generally aligned on a common longitudinal axis;

at least one connecting element for interconnecting the cylindrical elements, the at least one connecting element configured to interconnect only the cylindrical elements that are adjacent to each other;

the plurality of cylindrical elements formed into a serpentine pattern including a plurality of peaks and valleys;

the stent further being constructed of deforming components that undergo deformation upon expansion of the stent and components that remain undeformed upon expansion of the stent; and a radiopaque material affixed exclusively to the undeformed components of the cylindrical elements so that the radiopaque material is visible under fluoroscopy and the stent can be easily located in the body lumen.

9. The stent of claim 8, wherein the radiopaque material comprises a metal selected from the group of metals consisting of gold, platinum and silver.

10. The stent of claim 8, wherein the radiopaque material has a thickness in the range of approximately 0.0003 to 0.003 inch.

* * * * *

UNITED STATES PATENT AND TRADEMARK OFFICE
CERTIFICATE OF CORRECTION

PATENT NO. : 5,725,572
DATED : March 10, 1998
INVENTOR(S) : Sharon S. Lam, et. al.

It is certified that error appears in the above-identified patent and that said Letters Patent is hereby corrected as shown below:

The Title page should be deleted and substitute therefor the attached Title page.

Drawings:

Delete Figure Sheets 1 of 3 and 2 of 3, and substitute therefor sheets 1 of 3, and 2 of 3 as shown on the attached pages.

Signed and Sealed this

Twenty-sixth Day of September, 2000

*Attest:*

Q. TODD DICKINSON

*Attesting Officer*  *Director of Patents and Trademarks*

United States Patent [19]
Lam et al.

[11] Patent Number: 5,725,572
[45] Date of Patent: Mar. 10, 1998

[54] RADIOPAQUE STENT

[75] Inventors: Sharon S. Lam, San Jose; John J. Frantzen, Copperopolis, both of Calif.; Farhad Khosravi, Newton, Mass.

[73] Assignee: Advanced Cardiovascular Systems, Inc., Santa Clara, Calif.

[21] Appl. No.: 908,906

[22] Filed: Aug. 8, 1997

Related U.S. Application Data

[63] Continuation of Ser. No. 564,936, Nov. 30, 1995, abandoned, which is a continuation of Ser. No. 233,046, Apr. 25, 1994, abandoned.

[51] Int. Cl.$^6$ ............................................. A61F 2/06
[52] U.S. Cl. ........................... 623/1; 623/12; 606/191; 600/3
[58] Field of Search ..................... 623/1, 12; 606/191, 606/194, 198; 600/3

[56] References Cited

U.S. PATENT DOCUMENTS

| | | |
|---|---|---|
| 4,681,110 | 7/1987 | Wiktor . |
| 4,699,611 | 10/1987 | Bowden ............................ 604/51 |
| 4,718,907 | 1/1988 | Karwoski et al. . |
| 4,733,665 | 3/1988 | Palmaz . |
| 4,739,762 | 4/1988 | Palmaz . |
| 4,776,337 | 10/1988 | Palmaz . |
| 4,886,062 | 12/1989 | Wiktor . |
| 4,943,346 | 7/1990 | Mattelin . |
| 5,047,050 | 9/1991 | Arpesani .......................... 623/1 |
| 5,102,417 | 4/1992 | Palmaz . |
| 5,104,404 | 4/1992 | Wolff .............................. 623/1 |
| 5,222,971 | 6/1993 | Willard et al. ..................... 606/198 |
| 5,269,802 | 12/1993 | Garber ............................ 623/1 |
| 5,282,823 | 2/1994 | Schwartz et al. ................... 606/198 |
| 5,364,354 | 11/1994 | Walker et al. ..................... 604/96 |
| 5,423,849 | 6/1995 | Engelson et al. ................... 606/191 |
| 5,514,154 | 5/1996 | Lau et al. . |
| 5,562,728 | 10/1996 | Lazarus et al. .................... 623/1 |
| 5,649,952 | 7/1997 | Lam .............................. 623/12 |

FOREIGN PATENT DOCUMENTS

| | | |
|---|---|---|
| 0 380 668 A1 | 8/1990 | European Pat. Off. . |
| 0 517 075 A1 | 12/1992 | European Pat. Off. . |
| 0 540 290 A2 | 5/1993 | European Pat. Off. . |
| 2677872 | 12/1992 | France . |

*Primary Examiner*—Paul B. Prebilic
*Attorney, Agent, or Firm*—Fulwider Patton Lee & Utecht, LLP

[57] ABSTRACT

A radiopaque marker associated with a stent which is adapted to be implanted into a patient's body lumen to maintain the patency thereof and a convenient and accurate method for affixing the radiopaque marker to the stent. The radiopaque marker defining an acceptable profile and capable of facilitating, under fluoroscopy, the identification of the position, diameter and length of a stent without obscuring the lesion being repaired and without impeding the deformation of an expandable stent.

10 Claims, 3 Drawing Sheets